United States Patent [19]

Singer

[11] Patent Number: 5,824,787
[45] Date of Patent: Oct. 20, 1998

[54] POLYNUCLEOTIDE SIZING REAGENT

[75] Inventor: Paul A. Singer, Del Mar, Calif.

[73] Assignee: Gensura Laboratories, Inc., Del Mar, Calif.

[21] Appl. No.: 597,467

[22] Filed: Feb. 2, 1996

Related U.S. Application Data

[63] Continuation of Ser. No. 161,901, Dec. 3, 1993, abandoned.

[51] Int. Cl.$^6$ ............................ C07H 21/04; C12N 15/74
[52] U.S. Cl. ...................... 536/22.1; 536/25.4; 435/320.1
[58] Field of Search .................. 536/22.1, 25.4; 435/320.1

[56] References Cited

U.S. PATENT DOCUMENTS

| | | | |
|---|---|---|---|
| 4,994,368 | 2/1991 | Goodman et al. | 435/6 |
| 5,089,406 | 2/1992 | Williams et al. | 435/172.3 |
| 5,206,137 | 4/1993 | Ip et al. | 435/6 |
| 5,302,510 | 4/1994 | Klevan | 435/6 |

OTHER PUBLICATIONS

Hanlon et al. Nuc. Acids Res 17(13):5413 (1989).

Sigma Chemical Co. Catalog. 1991 pp. 1268 & 1269.

Webster's II New Riverside University Dictionary, 1984, p. 639.

*Primary Examiner*—Stephanie W. Zitomer
*Attorney, Agent, or Firm*—Fish & Richardson, P.C.

[57] ABSTRACT

A polynucleotide marker reagent is described for use in DNA and RNA size determination.

29 Claims, 4 Drawing Sheets

1. Uncloned ladder subunits; ladder generated only by ligation:

<u>20-mer</u>
NNN (N14) NNN
NNN (N14) NNN

2. Cloned, <u>integral</u>, ladder-generating insert of concatamerized subunits with unique restr. sites; ladder generated by partial restr. digestion of vector+insert.

<u>20-mer</u>             <u>100-mer</u> a) Midpoint restr. sites    (N7) GGATCC (N7):(N7) GGATCC (N7)
                           (N7) CCTAGG (N7):(N7) CCTAGG (N7)    (substitute N47 for N7)

b) Terminal (or junctional) restr. or half-restr. sites
      GGATCC (N14) GGATCC (N14)
            (N14)CCTAGG (N14) CCTAGG    (substitute N94 for N14)
                   or
      TCC (N14) GGA:TCC (N14) GGA
      AGG (N14) CCT:AGG (N14) CCT 3. Cloned, <u>excisable</u>, ladder-generating insert as in #2 above; ladder generated by partial restr. digestion of insert only, after it is precisely excised and separated from vector.

a) Excision cassette method        b) Compatible L-G and excision/insertion sites

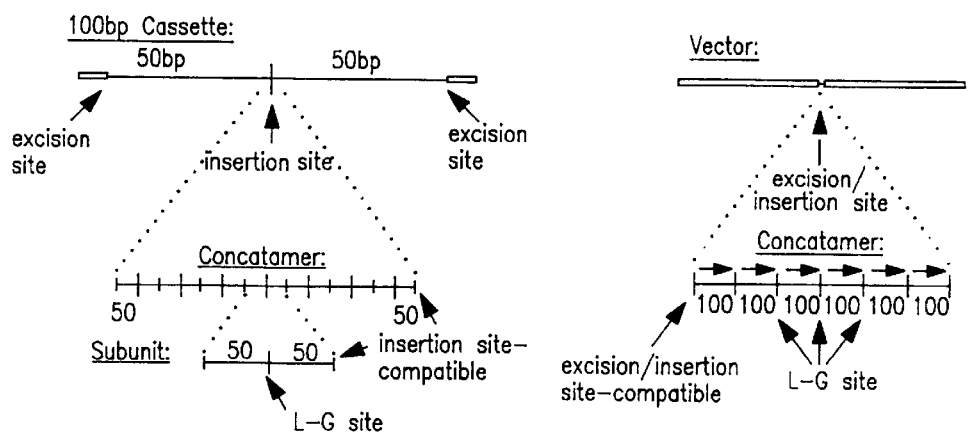

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: A ( i x ) FEATURE:
        ( A ) NAME/KEY: CDS
        ( B ) LOCATION: 1..20

( x i ) SEQUENCE DESCRIPTION: SEQ ID NO:1:

CTTGTGGGTG TGTTTGGTAG                              20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: A'

( i x ) FEATURE:
        ( A ) NAME/KEY: CDS
        ( B ) LOCATION: 1..20

( x i ) SEQUENCE DESCRIPTION: SEQ ID NO:2:

CTTGTGGGTG TGTTGGTTAG                              20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: A"

( i x ) FEATURE:
        ( A ) NAME/KEY: CDS
        ( B ) LOCATION: 1..20

( x i ) SEQUENCE DESCRIPTION: SEQ ID NO:3:

CTTGTGTGGG TGGTTTTGAG                              20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (i i) MOLECULE TYPE: DNA (genomic)

(v i i) IMMEDIATE SOURCE:
    (B) CLONE: R1D (i x) FEATURE:
    (A) NAME/KEY: CDS
    (B) LOCATION: 1..20

(x i) SEQUENCE DESCRIPTION: SEQ ID NO:4:

TTCGTGGGTG TGTTTGGTAG    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: R1P (i x) FEATURE:
        (A) NAME/KEY: CDS
        (B) LOCATION: 1..20

(x i) SEQUENCE DESCRIPTION: SEQ ID NO:5:

CTTGTGTGTG TTGGTGTGAA    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: Sm (i x) FEATURE:
        (A) NAME/KEY: CDS
        (B) LOCATION: 1..20

(x i) SEQUENCE DESCRIPTION: SEQ ID NO:6:

CTGGGGGCCC GGGTTTTTAG    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: HIII (i x) FEATURE:
        (A) NAME/KEY: CDS
        (B) LOCATION: 1..20

(x i) SEQUENCE DESCRIPTION: SEQ ID NO:7:

CTTGTGGGTG TGTTTTGAAG    20

( 2 ) INFORMATION FOR SEQ ID NO:8:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: ED ( i x ) FEATURE:
        ( A ) NAME/KEY: CDS
        ( B ) LOCATION: 1..10

( x i ) SEQUENCE DESCRIPTION: SEQ ID NO:8:

T T G T T G G T A G        10

( 2 ) INFORMATION FOR SEQ ID NO:9:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: EP ( i x ) FEATURE:
        ( A ) NAME/KEY: CDS
        ( B ) LOCATION: 1..10

( x i ) SEQUENCE DESCRIPTION: SEQ ID NO:9:

C T T G T G T G G G        10

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: EP/ED ( i x ) FEATURE:
        ( A ) NAME/KEY: CDS
        ( B ) LOCATION: 1..20

( x i ) SEQUENCE DESCRIPTION: SEQ ID NO:10:

C T T G T G T G G G  T T G T T G G T A G        20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SmD/ED ( i x ) FEATURE:
        ( A ) NAME/KEY: CDS
        ( B ) LOCATION: 1..20

( x i ) SEQUENCE DESCRIPTION: SEQ ID NO:11:

CTGGGGGCCC TTGTTGGTAG 20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: EP/SmP ( i x ) FEATURE:
        ( A ) NAME/KEY: CDS
        ( B ) LOCATION: 1..20

( x i ) SEQUENCE DESCRIPTION: SEQ ID NO:12:

GTTGTGTGGG GGGTTTTTAG 20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: PMR ( i x ) FEATURE:
        ( A ) NAME/KEY: CDS
        ( B ) LOCATION: 1..20

( x i ) SEQUENCE DESCRIPTION: SEQ ID NO:13:

CTGGCGCGGG GCATGACTCC 20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: T7

( i x ) FEATURE:
        ( A ) NAME/KEY: CDS
        ( B ) LOCATION: 1..20

( x i ) SEQUENCE DESCRIPTION: SEQ ID NO:14:

TATAGTGAGT CGTATTAAAG 20

( 2 ) INFORMATION FOR SEQ ID NO:15:

( i ) SEQUENCE CHARACTERISTICS:
        ( A ) LENGTH: 11 base pairs ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..11

( x i ) SEQUENCE DESCRIPTION: SEQ ID NO:15:

GGCCTCAAGA A 11

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..24

( x i ) SEQUENCE DESCRIPTION: SEQ ID NO:16:

CACACTTAAG TAGGTTCTAA TTTT 24

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:17:

TTACTTGTGT TTTGAAG 17

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..15

( x i ) SEQUENCE DESCRIPTION: SEQ ID NO:18:

GAACCTTTAG TTCTT 15

( 2 ) INFORMATION FOR SEQ ID NO:19:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear (i i) MOLECULE TYPE: DNA (genomic)

(i x) FEATURE:
    (A) NAME/KEY: CDS
    (B) LOCATION: 1..78

(x i) SEQUENCE DESCRIPTION: SEQ ID NO:19:

```
CATGTGGGTG  TGTTGGTTAG  CTGGCGCGGG  GCATGACTCC  TATAGTGAGT  CGTATTAAAG        60

CTTGAGTATT  CTATAGTG                                                         78
```

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: RNA (genomic)

(i x) FEATURE:
        (A) NAME/KEY: CDS
        (B) LOCATION: 1..40

(x i) SEQUENCE DESCRIPTION: SEQ ID NO:20:

```
GAACACCCACACAACCAAUCGACCGCGCCCCGUACUGAGG                                     40
```

POLYNUCLEOTIDE SIZING REAGENT

This is a continuation of application Ser. No. 08/161,901, filed Dec. 3, 1993, now abandoned.

BACKGROUND OF THE INVENTION

1. Field of the Invention

This invention relates to polynucleotide structures and specifically to a novel nucleic acid multimer which is useful for generating a size marker for DNA and RNA.

2. Description of Related Art

Nearly all scientific investigations involving nucleic acids use gel electrophoresis, primarily agarose gels, as a fundamental tool. Voltage applied at the ends of an agarose gel generates an electric field with a strength defined by the length of the gel and the potential difference at the ends. DNA or RNA molecules exposed to an electric field migrate toward the anode due to the negatively charged phosphates along the nucleic acid backbone. The size of the nucleic acid determines the rate at which it passes through the gel, thereby allowing an effective separation of fragment-length mixtures by electrophoresis. In order to effectively monitor the electrophoretic separation and results accurately interpreted, such tools as molecular weight size markers are typically used.

Among the samples analyzed on a gel, at least one lane should contain a series of nucleic acid fragments of known sizes such that a standard curve can be constructed to allow the calculation of the sizes of unknown nucleic acid fragments. The most commonly used DNA molecular weight markers are restriction digests of phage lambda DNA or, for smaller fragments, the plasmid pBR322.

Ladder markers for agarose gel analysis of double-stranded DNA are generally generated using three basic strategies: 1) ligation of uncloned subunits into concatamers; 2) partial restriction digestion of a vector and insert, where the insert is composed of concatamerized subunits; and 3) partial restriction digestion of an excised insert, composed of concatamerized subunits, but devoid of the plasmid DNA. In strategy 2, there are typically no ladder-generating restriction sites in the vector itself to interfere with the ladder structure, however, undigested vector DNA is still present at the top of the ladder structure.

Markers for denaturing acrylamide gel analysis of single-stranded (ss) DNA must, in general, be radioactively or non-radioactively labeled for detection in commonly used procedures. Restriction fragments or commercial ladders are end-labeled for this purpose, but the end-labeling and purification procedures are often considered to be inconvenient by researchers. The most common procedure in ssDNA analysis is DNA sequencing by dideoxy chain termination. The high resolution DNA "sequence ladder" thus obtained can serve adequately as markers. DNA sequence ladders are often generated and used by researchers as markers for other types of ssDNA analysis, such as primer extension experiments to map the 5' ends of mRNAs. Although they are easily generated, DNA sequence ladders nevertheless have some drawbacks as ssDNA size markers. In particular, the process of orientation within a DNA sequence is often tedious, involving detailed reading and re-reading of the sequence, knowledge of the exact priming site, and manual base counting, for example.

At present there are no adequate radiolabeled markers for the sizing of small RNAs. Regularly sized templates for use with RNA polymerases such as SP6, T3, or T7 promoters, for example, represent a logical source of such markers. A limited set of templates generating 100, 200, 300, 400, and 500 nucleotide bands have recently been synthesized, however, the need for finer ladder steps is critical for accurate sizing of smaller sized RNA fragments. Unlabeled RNA markers generated by in vitro synthesis or derived from naturally occurring mRNAs have been available for some time, however, these markers generally provide inadequate coverage of the low range RNAs. These markers also require tedious labeling to be useful in many applications. Such markers are routinely used in the higher ranges for sizing mRNA preparations or specific mRNAs detected by hybridization by Northern analysis, but even in the high range, these markers lack the coverage and resolution that would be provided by a 1000 or 500 base RNA ladder.

In view of the problems associated with the markers presently available and the lack of appropriate markers in some cases, it is apparent that there remains a need for improved markers to provide optimal resolution and ease-of-use in all size ranges and categories of nucleic acid analysis including gel electrophoresis of large and small dsDNA and ssDNA fragments and RNAs. The present invention fulfills this need.

SUMMARY OF THE INVENTION

The present invention provides a reagent for generating a nucleic acid size marker comprising a multimer with about 100 to about 1000 nucleotides per strand. The multimer comprises repeats of subunits which contain a distinctive nucleotide pattern which defines regular intervals in the multimer. Each oligonucleotide subunit has a purine and pyrimidine content of about 50% each per subunit and each oligonucleotide unit is substantially non-self-complementary. Preferably, the regular intervals within the subunits are the length in nucleotides, of a whole integer which is a divisor of 100, and most preferably the regular intervals are a length selected from the group consisting of 5, 10, 20, and 25 nucleotides.

The reagent may further comprise a selectable cleavage site located at the junction between the regular intervals. A second selectable cleavage site may also be located at the junction between the regular intervals at the nth nucleotide, where n is divideable by 100 or 100 is a divisor of n. The selectable cleavage site is preferably a restriction endonuclease site.

The reagent may further comprise an additional 5'-terminal or 3' terminal oligonucleotide unit wherein the additional unit has a different sequence from the subsequent oligonucleotide units. For example, the 5' oligonucleotide unit may contain an RNA polymerase promoter and the 3' oligonucleotide may contain a primer binding site.

BRIEF DESCRIPTION OF THE DRAWINGS

FIG. 1 shows a schematic illustration of strategies for generating double-stranded ladders.

FIG. 2a shows synthesis of the upper strand with five 20 nucleotide elements, R1D/A/Sm/A'/R1P.

FIG. 2b shows the 100-mer cassette of FIG. 2a cloned into the EcoRI site of PUC19*.

FIG. 2c shows cloning of a dimer of the sequence derived from FIG. 2b, cloned into the SmaI site of the cassette.

FIG. 2d shows the pUC19*-ds300 containing three 100-mer subunits.

DETAILED DESCRIPTION OF THE INVENTION

Figure 2:
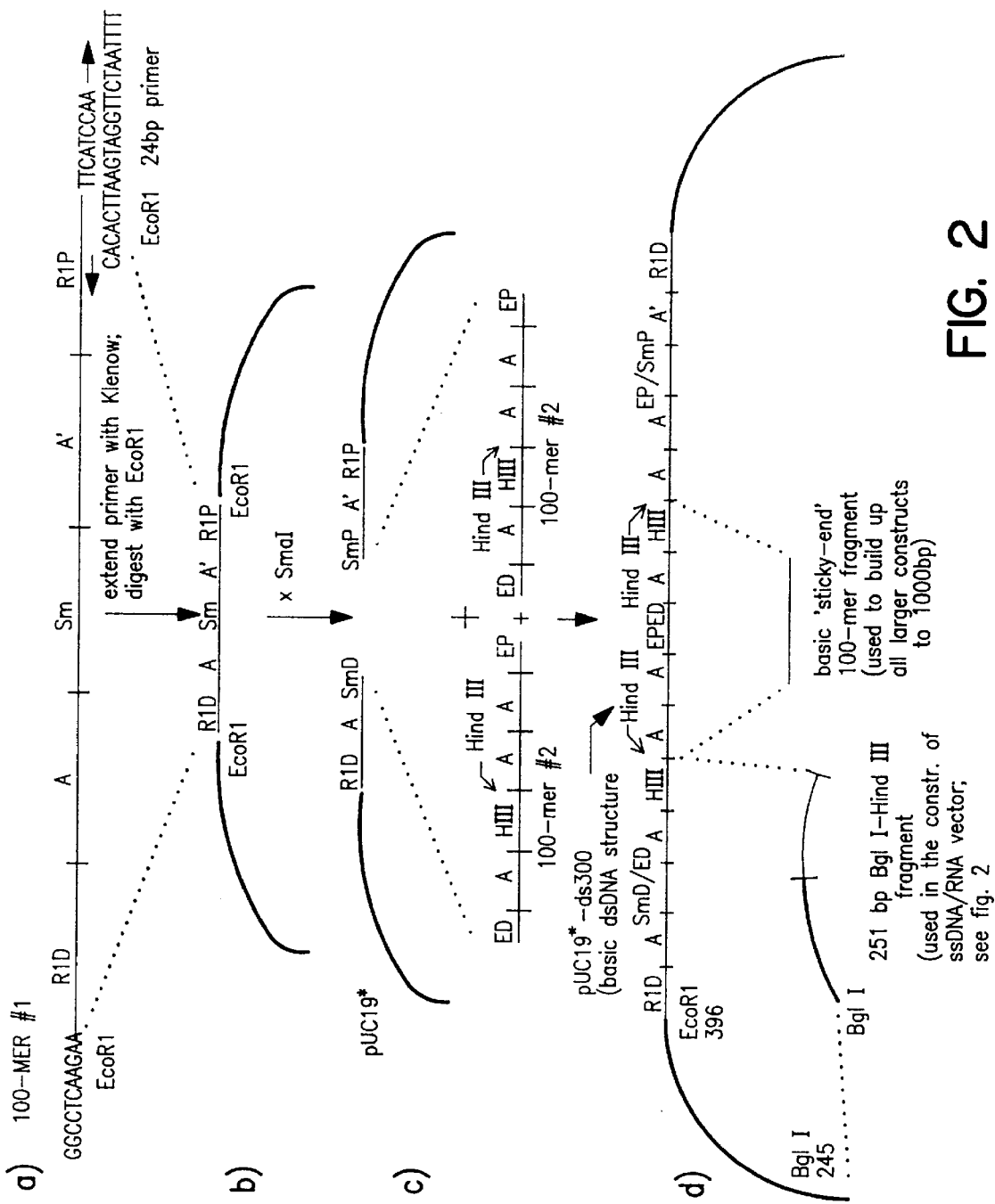
FIG. 2 shows the construction, structure, and cloning of a precisely excisable concatameric insert for the generation, by partial restriction digestion, of both 100 bp and 20 bp dsDNA ladders (SEQ ID NOS: 15 and 16).

The present invention provides a reagent for generating a nucleic acid size marker comprising a nucleic acid multimer having about 100 to about 1000 nucleotides. The reagent functions as a template for generating RNA or single-stranded (ss) DNA size marker ladders. The reagent itself may also be useful for the generation of a double-stranded DNA ladders. The multimer comprises repeats of substantially identical oligonucleotide subunits wherein a distinctive pattern within the subunits defines regular intervals. The nucleic acid reagent has a purine and pyrimidine content of about 50% each per interval and has nucleotides on a single strand which are substantially non-self-complementary. Preferably, the regular intervals within the multimer are a length, in nucleotides, of a whole integer which is a divisor 100, and most preferably the regular intervals are a length selected from the group consisting of 10, 20, and 25 nucleotides.

As referred to herein, the multimer reagent will be considered to be in the double-stranded (ds) DNA form, wherein the nucleotide composition and organization referred to are those of one single strand of the dsDNA reagent. The multimer reagent template may also exist in ssDNA or RNA form, from which ssDNA, RNA or dsDNA ladders can be derived. A number of techniques exist for synthesizing nucleic acids in one form or another (i.e. dsDNA, ssDNA, and/or RNA) and/or converting them between forms, and these are generally known to those skilled in the art. Such techniques include, but are not necessarily limited to denaturation; expression in filamentous ssDNA-producing phage such as M13; primer-dependent DNA synthesis; polymerase chain reaction (PCR) or other forms of cycling amplification; transcription and reverse transcription; and chemical synthesis.

As used herein, the term "oligonucleotide" refers to a molecule comprised of two or more deoxyribonucleotides or ribonucleotides. Preferably the oligonucleotide subunits of the invention are ten or greater nucleotides. Each "subunit" contains a sequence of nucleotides which contain the characteristic nucleotide pattern described herein. The subunits are of distinctive length, composition and organization of nucleotide bases so as to provide a template for the synthesis of RNA and ssDNA molecules which are non-self annealing of approximately equal purine/pyrimidine content, and which can express the regular intervals of the multimer reagent by chain termination products according to standard in vitro RNA transcription or DNA sequencing protocols performed in the presence of 3'deoxy NTP or dNTP nucleotides, respectively.

The reagent has oligonucleotide subunits attached head-to-tail. The term "head-to-tail" refers to the 5'-terminal end of each subunit being attached with and lying adjacent to the 3'-terminal end of the preceding subunit. Therefore, all subunits extend 5' to 3'. The multimer of the invention may be concatamerized to form a reagent of the length desired.

The reagent of the invention may be DNA or RNA and may be single-stranded (ss) or double-stranded (ds). Therefore, the nucleic acid multimer of the invention may be ssDNA and further comprise a second DNA strand which is complementary to a single-stranded multimer.

The individual oligonucleotide subunits of the multimer contain a distinctive nucleotide pattern, wherein the pattern defines regular intervals in the multimer. This nucleotide pattern comprises "interval-determining" nucleotides. The multimer is a polymer of the same repeating oligonucleotide unit or different oligonucleotide units. Each subunit, and the regular intervals of the generated RNA, ssDNA, or dsDNA ladders derived therefrom, will typically be from about 5 to about 25 nucleotides in length. The distinctive nucleotide pattern is characterized by having a single, specific nucleotide (typically either adenine, A; guanine, G; cytosine, C; or thymidine, T), which is represented only once, at the same relative position, in each subunit, wherein regular intervals between such specific nucleotides result which are equal in length to the length of the subunit. The distinctive pattern may also be a di- or tri-nucleotide pattern which defines the regular intervals and subunits, and is termed the "interval-determining" nucleotide(s). It is preferable that a single unique residue define the regular intervals.

The distinctive nucleotide pattern of the subunits is further characterized in that the positions in the subunit that are not the interval-determining unique nucleotide(s) are occupied entirely by nucleotide bases, hereinafter termed "filler" bases, belonging to that set of non-complimentary purine (pu) and pyrimidine (py) nucleotides (i.e., either Gs/Ts or As/Cs) which does not include the specific nucleotide of the unique position.

In addition, each oligonucleotide subunit within the multimer contains a balance of purines and pyrimidines such that an average standard mobility for the RNA and DNA embodiments of the invention, and of all partial RNA and ssDNA embodiments terminated at the "interval-determining" nucleotides, is attained. For example, if the subunit contains 48% purines, it must, by definition contain 52% pyrimidines. In addition to the commonly known purine deoxyribonucleotides, adenine (A) and guanine (G), and the pyrimidines, thymine (T) and cytosine (C), the nucleotides of the multimer may include nucleotide analogs, including such nucleotides as inosine (I). Other nucleotide analogs will be known to those of skill in the art.

The multimer comprises at least one single-stranded nucleotide sequence which is substantially non-complementary, or non-self annealing with the sequence on that strand or within an individual subunit. For example, a subunit may be comprised predominantly of Gs and Ts (as opposed to As and Ts) as fillers if the unique residue is C; As and Cs (as opposed to Gs and Cs) if the unique residue is T; Gs and Ts (as opposed to Gs and Cs) if the unique residue is A; and As and Cs (as opposed to As and Ts) if the unique residue is G. In this manner, a stable "hairpin" configuration will not form and the nucleotide sequence of the RNA or DNA will remain linear.

The stipulation for the nucleotide pattern of the subunits allows for the possibility of a second unique nucleotide (or di or tri nucleotide) to exist at a different position within the subunit. For example, a subunit may have a unique A and a unique C residue, and be otherwise comprised of filler G and T residues. Under these conditions the stipulations of non-complimentarity and approximately equal purine (pu) and pyrimidine (py) bases can still be met for each subunit; however it should be noted that non-complimentarity will be somewhat less stringent in this case, and progressively less stringent if di- or tri-nucleotides exist at such unique positions. One or the other of these unique positions can be designated as the 'interval-determining' position; wherein it would be desirable that the register of RNA polymerase promoter and primer binding elements is adjusted accordingly (see below). In contrast, it is evident that no more than two unique base positions can exist in the subunits while still meeting the above stipulations, since use of a third base in a unique position would only leave one base for the remaining filler positions of the subunit, with no possibility of achieving non-complimentarity and equal pu and py content within the subunit. The use of nucleotide analogs such as inosine (I) in addition to the four standard bases is possible, and would alter these considerations in ways which are self-evident.

The multimer reagent may further comprise one or more selectable cleavage sites at various positions within (or at the junctions of) its constituent subunits. Such sites can provide an alternative method of generating RNA and ssDNA ladders with intervals equal to the length of the subunits, according to the invention. Such selectable cleavage sites can also provide a method for generating a dsDNA ladder from the multimer reagent. In this case, the dsDNA multimer reagent does not function as a template, but is itself (after suitable amplification by cloning) the material for the ladder. A slightly modified subunit nucleotide pattern, still adhering to the stipulations of substantial non-complimentarity and approximately equal pu/py content, may be used every nth subunit, or at the 5'-and 3'-termini of the multimer, wherein such a pattern would specify a different cleavable site (or junctional half-site), not present in the other subunits of the multimer. For example, there may be a selectable cleavage site formed at the junction of every 20 nucleotide (nt) subunit, and a different half-site at the junctions of the 100 nucleotide multimer. Head-to-tail concatamerization of the multimer would then generate the second cleavable site and allow both 20 nt and 100 nt subdivisions to be generated from the same reagent. Preferably such selectable cleavage sites would be restriction endonuclease sites, wherein partial digestions of such sites can be used to generate ladders containing varying sizes of the marker.

Many different palindromic restriction endonuclease sites can be constructed in the region of the 'interval-determining' nucleotides of the subunits. For example, sites like CCGG, which is the recognition sequence for the restriction endonuclease Hpa II, can be constructed around a unique dinucleotide at the interval-determining position. Sequences like AGCT, GATC, TCGA, and GTAC, recognition sequences for the restriction endonucleases A/u I, Sau 3A, Taq I, and Rsa I, respectively, can be constructed where two unique residues (e.g., A and C) exist one base apart, with the remaining positions occupied appropriately by filler bases (e.g., G and T). The reagent may further comprise a selectable cleavage site located at the junction between regular intervals. A second selectable cleavage site may also be located at the junction between the intervals at a sequence of every nth nucleotide, where n is a divisor of 100. Therefore, there may be a specific cleavable site located at every subunit and a second site located after every 100th nucleotide, allowing different size ladders to be generated. The selectable cleavage site is preferably a restriction endonuclease site.

Nonpallindromic or degenerate-sequence restriction endonuclease sites can also exist in interval-determining regions of each subunit, as well as entirely within filler regions of the subunit. For example, the restriction endonuclease Mnl I recognizes the sequences 5'-CCTC-3' and 5'-GAGG-3', which could be present within subunits having C/T or A/G filler bases, respectively. Other restriction endonucleases in these latter categories, as well as other examples of palindromic sites which can be constructed within the stipulations of the subunit structure, will be known to those of skill in the art (See for example, *Current Protocols in Molecular Biology*, Wiley Intersciences, eds. Ausubel, et al, 1993, sec. 3.1.10).

For the purpose of generating RNA and ssDNA ladders, the multimer reagent is used in conjunction with an RNA polymerase promoter element and a priming site for primer-dependent DNA synthesis, respectively. The RNA polymerase promoter and primer-binding elements may be located either upstream (at the 5'-terminal end) or downstream (at the 3'-terminal end) of the multimer, directing synthesis of the plus (upper) or minus (lower) strand of the multimer, respectively. The RNA polymerase promoter is preferably a bacteriophage promoter such as T3, T7, or SP6, for example (Parvin, et al., DNA 3:167, 1986). The T7 bacteriophage RNA polymerase specifically initiates transcription at a 23 nucleotide promoter sequence which has a G residue at its 3'-terminal end that becomes the 7m-G cap nucleotide at position 1 of the synthesized RNA molecule. Expression systems in *E. coli* and in vitro have been developed based on these bacteriophage promoters, i.e., by cloning the DNA sequence to be transcribed adjacent to the promoter sequences so that efficient transcription of the DNA occurs (Tabor, et al., *Proc. Natl. Acad. Sci. USA*, 84:4767, 1985; Rosenberg, et al., Gene, 56:125, 1987; Studier, et al., *Methods Enzymol*, 185, 1990). The priming site may be the same sequence, or included as part of the sequence, of the RNA polymerase promoter element, alternatively it may be a different sequence that satisfies the positional requirements described herein.

The location of the RNA polymerase promoter and primer binding sites in relation to the interval-determining, nucleotide(s) of the subunits is important for generating optimal size ladders according to the invention. The relevant residues are the RNA initiation site (RNA-IS) of the RNA polymerase promoter, and the 5'-terminus of the oligonucleotide primer used in conjunction with the primer binding site, respectively. Preferably, these promoter or binding site residues should be in "register" with the interval-determining nucleotides of the subunits; such register being determined in relation to the length of the subunits. The term "register" is meant to indicate that the residues are the same (or exact multiple) distance from the interval-determining nucleotide as the latter are from each other. For example, with multimer subunits of 20 nt, the RNA-IS and primer terminus residues should preferably be in a position 20 nt distant (or, less preferably, 40, 60, 80 nt, etc.) from the interval-determining nucleotide of the most proximal subunit of the multimer. In this manner, the generated ladders will have steps equivalent to exact multiples of the subunit length, e.g. 20, 40, 60, 80 nt, etc. Undesirable locations of the RNA initiation site and primer 5'-terminus, i.e. those not in register as described above, would generate a ladder with steps that are not exact multiples of the subunit length, e.g. 21, 41, 61, 81 nt, etc.

To achieve the register described above, the multimer reagent may be inserted (i.e. cloned) into the appropriate position in the polylinker of a plasmid or phage vector such as M13, wherein the polylinker is flanked by T7, SP6, or T3 bacteriophage RNA polymerase promoters to be used in the generation of the RNA ladder. Such promoter elements may also function as primer binding sites for primer-dependent DNA synthesis to be used in the generation of the ssDNA ladder. Alternatively, priming sequences may be chosen which are completely independent of the promoter elements. Attainment of the proper register may also involve the prior cloning of a spacer oligonucleotide 'cassette' into the polylinker, or the inclusion of spacer nucleotides or functional promoter and primer-binding elements in a special 'cassette' version of the multimer reagent itself. These vectors, promoters and techniques for achieving control of spacing and register of the inserted multimer, as well as other vectors, promoters and techniques for achieving the same purpose, are generally routine in nature and will be known to those of skill in the art.

According to the preferred method for generating RNA and ssDNA sizing ladders, the bacteriophage RNA polymerase promoters and/or oligonucleotide primer binding sites are utilized for in vitro 3'dNTP mediated, chain-termination sequencing systems (Current Protocols in Molecular Biology, Ausubel, et al., supra). Specifically, the 3'dNTP reaction utilized (either 3'dATP, -dGTP, -dCTP, or -dTTP) is the one corresponding to the interval-determining nucleotide of the subunits in register, as described above, with the RNA-IS or 5'-terminus of the oligonucleotide DNA primer, respectively. "Corresponding" in this case refers to the complimentary base to the "interval-determining" nucleotide in the template strand of the multimer reagent. In the case of generating a ssDNA ladder, the reaction is identical, or essentially identical, to those described by Sanger, et al., which are commonly used for dideoxy sequencing of DNA. For RNA, a similar 3'-deoxy based system has also been described (Parvin, et al, *DNA* 5(2):167, 1986), which involves bacteriophage promoter-driven RNA transcription in the presence of the four nucleoside triphosphates (NTPs; ATP, GTP, CTP, and TTP). One exception has been noted by Parvin, et al. supra, involving the substitution of inosine-triphosphate (ITP) for GTP in the reaction. In this procedure, appropriate quantities (20–600 $\mu$M) of the 3'-deoxy NTP are incorporated in the reaction mixture from the start, as contrasted with the Sanger dideoxy DNA sequencing protocol which typically adds the dideoxy dNTPs after an initial chain elongation step.

An alternative method for generating the RNA and ssDNA ladders is standard promoter-driven RNA synthesis or primer-dependent DNA synthesis. This is performed on the multimer reagent template which had been first subjected to stepwise truncation by partial digestion at restriction endonuclease sites corresponding to the interval-determining positions of the subunits. Preferably, this method would be employed to accentuate the larger subdivisions of the ladders (e.g., the 100 nt divisions).

A second alternative method for generating the RNA ladder may involve the partial digestion of the full-sized RNA derived from the multimer reagent template using a base-specific endo-ribonuclease. An example would be the use of RNase T1, which cleaves ribonucleic acids at the 3' side of every GTP residue. Other examples of base-specific endo-ribonucleases will be known to those skilled in the art. A prerequisite for such a procedure is that the interval-determining nucleotide be only a mononucleotide, rather than a homo di- or tri-nucleotide; otherwise RNA digestion would create (n-1)- or (n-2)-sized intervals, respectively. Another prerequisite is that the interval determining nucleotide cannot be represented at any other position within the subunit other than the interval-determining position. In this regard, it is noted that the initiation GTP residue of the synthetic RNA molecule would constitute a non-interval-determining position, wherein partial digestion with RNase T1 would cause double bands to occur at every step in the ladder. A further prerequisite is that the multimer reagent template must be truncated uniquely at its distal end, wherein such truncation must be in precise register with the intervals of the subunits of the multimer; otherwise a superimposed pattern would result, in which a second band would be present in each interval, equal in intensity to the interval-determining band, and at a distance apart from that band corresponding to the number of residues the truncated full size RNA differs from the preferred full-size RNA described above.

A method for generating a double-stranded (ds) DNA ladder from the multimer reagent has been mentioned above. This method involves the use of the multimer reagent itself to form the substance of the ladder, not indirectly as a template for ladder synthesis as in the case of RNA and ssDNA ladders. For this purpose, the ladder reagent, or concatamerized multimers thereof, is amplified by cloning in an appropriate vector (e.g. plasmid, phage), wherein the recombinant vector-insert DNA is treated by partial digestion at the interval-determining restriction endonuclease sites of the subunits, and those of the nth subunits or multimer-termini to produce the ladder. Alternatively, concatamerized multimers of the ladder reagent may be cloned within an excisable cassette, which is purified from the vector before use in generating the ladder.

Other techniques may exist, and are known to those skilled in the art, for utilizing the multimer reagent template (and, in particular, RNA or ssDNA embodiments of the multimer reagent template) in the preparation of RNA, ssDNA, or dsDNA ladders. Such techniques include, but are not necessarily limited to: denaturation; expression in filamentous ddSNA-producing phage like M13; primer-dependent DNA synthesis; promoter oligonucleotide annealing; polymerase chain reaction (PCR) or other forms of cycling amplification; transcription and reverse transcription; and chemical synthesis.

The multimer reagent of the invention may be labeled. There are many different labels and methods of labeling known to those of ordinary skill in the art. Examples of the types of labels which can be used in the present invention include radioisotopes, fluorescent compounds, colloidal metals, chemiluminescent compounds, phosphorescent compounds, and bioluminescent compounds. Those of ordinary skill in the art will know of other suitable labels for use with the reagent, or will be able to ascertain such, using routine experimentation.

The multimers of the invention may be prepared by cloning, enzymatic assembly, chemical cross-linking techniques, direct chemical synthesis or a combination thereof. Nucleic acid sequences that encode the entire multimer or fragments thereof can be made in single- or double-stranded form by conventional cloning procedures. The multimer/fragments can be made in double-stranded form and denatured to provide single-stranded multimers/fragments. Multimers may be cloned in single-stranded form using conventional single-stranded phage vectors such as M13. Fragments can be linked enzymatically or chemically to form the multimer. When assembled enzymatically, the individual units are ligated with a ligase such as T4 DNA ligase.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

For example, one of the container means may comprise the nucleic acid multimer which is or can be detectably labelled. A second container may contain at least one 3'-deoxy NTP or dNTP. For example, the specific 3'-deoxy dNTP of the interval-determining nucleotide(s) would be utilized in the Sanger dideoxy sequencing technique for generating a ssDNA ladder. Alternatively, a second container may comprise enzymes, such as a restriction enzyme or RNase.

The above disclosure generally describes the present invention. A more complete understanding can be obtained by reference to the following specific examples which are provided herein for purposes of illustration only and are not intended to limit the scope of the invention.

EXAMPLE 1

DESIGN OF BASIC SEQUENCE ELEMENTS FOR THE CONSTRUCTION OF dsDNA, ssDNA, AND RNA 100 bp/20 bp LADDERS

A starting point for the design of a 100 nucleotide plus 20 nucleotide (100 nt/20 nt) ladder template was the synthesis of 100-base oligomers composed of tandem repeats of prototypic 20 nt subunit elements. These subunit elements incorporate the "interval-determining" nucleotide and a selectable palindromic restriction endonuclease site, as described herein, at their terminal (or junctional) positions. The 100-base oligomers were then be made double-stranded and ultimately concatamerized and cloned to create the required larger ladder structures (i.e., 1000 bp and 5000 bp). Three such 100-mers were eventually synthesized (referred to as 100-mers #1, #2, and #3-T7 in Table 1 and FIGS. 2 and 3). These 100-mers also contain derivatives of the prototypic 20 nt subunits, for the purpose of incorporating specific additional features. These include: 1) subunits to create a modified multimer reagent used as an excision-cassette (as in FIG. 1, #3a) for the dsDNA ladder (100-mer #1); 2) subunits for a 100-mer (100-mer #2) which could integrate into the excision cassette and, additionally, incorporate a different restriction endonuclease site every 100 nt; and 3) subunits to create a modified "cassette" version of the multimer reagent (100-mer #3+T7) containing primer binding and T7 promoter regions with their respective primer 5'-terminus and RNA-IS corresponding to base #1 of the multimer cassette. These subunits are listed in Table 1.

The advantage of the first strategy is that no special structural features are required (i.e. no restriction sites necessary). The disadvantage is that it requires uncloned source of subunits, which is practical only for smaller subunits (e.g. 10-, 20-, 25-mers) by oligonucleotide synthesis. In strategy 2, ladder-generating (L–G) restriction sites must be at the midpoint (a) or formed symmetrically at the precise terminus of each subunit, whether it is a cohesive or blunt-end terminus (b). (In the unusual case where the L–G sites are asymmetrically located in the subunits perfect head-to-tail concatamers are required.) L–G sites must not be present in the vector, unless the partial restriction fragments generated will not interfere with the ladder which is almost impossible to achieve. The advantage is with cloned DNA as a source, the subunit size is not restricted to small oligomers. A disadvantage is that even if no L–G sites are present in the vector, the vector DNA will still be present as a thick, overloaded band at the top of the ladder. In strategy 3, for excision cassette method (a) 100 bp cassette has insertion site at the midpoint, with half a subunit length on each side subunit termini are compatible with insertion site (e.g., blunt-ended), and the L–G site is at the midpoint of each subunit. Insertion site is not regenerated (or not used). For the 'compatible . . . method' (b) L–G sites must be half-sites of the excision insertion site (e.g., half-BamH1 (GGATCN or NGATCC] and full BamHI [GGATCC] resp). Subunits must be concatamerized head-to-tail so as to regenerate excision insertion site at any internal positions. The advantages are elimination at overloaded vector DNA band from ladder wider choice of restriction enzymes to generate ladder since vector sites do not interfere excised ladder inserts can themselves be concatamerized to form compound concatamers for easier generation of extended size ladders.

As exemplified by the prototypic A, A', or A" elements shown in Table 1, the essential feature common to all the 20 nt elements is that they are composed of equal numbers of purines (A+G) and pyrimidines (C+T), in accordance with the criteria described herein. With the exception of Sm, its fusion derivative, SmD/Ed, and PMR, all the elements are also composed entirely of one set of non-self annealing purine-pyrimidine (Pu-Py) pairs (in this case G-T) in the internal 16 nt positions. Sm and SmD/ED have C substituted for T in some positions as a result of creating a SmaI site [CCCGGG] for the excision cassette structure; PMR has other substitutions, including As for some Gs, designed to make it a unique primer-binding sequence. The terminal (or junctional) dinucleotides in the prototypic elements are CT . . . AG—a sequence motif which creates AluI sites (AGCT) every 20 nt within the basic 100-mer subunits. AluI sites were chosen for the generation of the 20 nt intervals because they contain all four bases, which allows flexibility in the choice of 3'deoxy ssDNA and RNA termination points. It should be noted that numerous other combinations of restriction sites and non-self annealing Pu/Py bases could have been chosen to meet the above criteria (e.g. Sau3a [GATC], TacI [TCGA], or other such sites together with either A-C or G-T pairs in the 16 nt internal positions). Exceptions to the terminal AluI site-generating dinucleotides are found in: i) the terminal AAG of the HIII element, which forms the HindIII site, AAGCTT, used to generate the 100 nt steps in the ladder (it also still forms AluI site); and ii) the elements R1D and R1P, which form part of EcoRI sits, GAATTC, used at the extreme outside termini of 100-mer #1 to excise larger built-up ladder inserts. Since the strategy used herein entails excision and purification of the insert in the preparation of the dsDNA ladder, the presence of AluI sites in the vector was not a negative factor. Moreover, vector AluI sites also do not interfere with primer extension or in vitro RNA transcription used for the ssDNA and RNA ladders, respectively.

TABLE 1

SEQUENCES AND DESCRIPTIONS OF 20nt ELEMENTS

| Element Designation | Sequence | Description of Features | Base Ratios |
|---|---|---|---|
| A<br>Basic 20-mer subunit | A(m1)<br>CTTGTGGGTGTGTTTGGTAG | G + T >> A + C; 5' end is half-AluI (and Hind III) site; 3' end is also half-AluI site. | A + G = 10<br>G + C = 10 |
| A'<br>same as A; found only once in pos. 21–40 of 100-mers #1 & #3 | A(m2)<br>CTTGTGGGTGTGTTGGTTAG | Base changes inadvertent; no functional significance | A + G = 10<br>G + C = 10 |
| A"<br>Used in synth. 100-mer #3 as replacement for EP/SmP. | CTTGTGTGGGTGGTTTTGAG | Base changes inadvertent; no functional significance | A + G = 10<br>G + C = 10 |
| R1D<br>Distal EcoRI subunit of synth. 100-mer #1 | TTCGTGGGTGTGTTTGGTAG | 5' end changed to half-EcoRI site. | A + G = 10<br>G + C = 10 |
| R1P<br>Proximal EcoRI subunit of synth. 100-mer #1 | CTTGTGTGTGTTGGTGTGAA | 3' end changed to half-EcoRI site. | A + G = 10<br>G + C = 9 |
| Sm<br>SmaI-containing subunit of synth. 100-mer #1 | CTGGGGGCCCGGGTTTTTAG | Base changes to create SmaI site in center. Other changes not functional. | A + G = 10<br>G + C = 13 |
| HIII<br>Hind III subunit of synth. 100-mer #2 | CTTGTGGGTGTGTTTTGAAG | 3' end changed to half-Hind III site. | A + G = 10<br>G + C = 9 |
| ED<br>Distal end of synth. 100-mer #2 | TTGTTGGTAG | 10bp end required in order to have Hind III site in center of 100-mer. | A + G = 5<br>G + C = 4 |
| EP<br>Prox. end of synth. 100-mer #2 | CTTGTGTGGG | 10bp end required in order to have Hind III site in center of 100-mer. | A + G = 5<br>G + C = 6 |
| EP/ED<br>Proximal End/Distal fusion product (of synth. 100-mer #2) | CTTGTGTGGGTTGTTGGTAG | 20-mer subunit (EP + ED) from blunt head-to-tail ligation of synth. 100-mer #2. | A + G = 10<br>G + C = 10 |
| SmD/ED<br>Distal Half of SmaI subunit fused with distal end of synth. 100-mer #2 | CTGGGGCCCTTGTTGGTAG | Result of blunt-end head-to-tail ligation of 2x(synth. 100 mer #2) into SmaI site of synth. 100-mer #1. | A + G = 10<br>G + C = 13 |
| EP/SmP<br>Proximal End of synth. 100-mer #2 fused with proximal half of SmaI subunit | GTTGTGTGGGGGTTTTAG | Same as above. | A + G = 10<br>G + C = 10 |
| PMR<br>Primer-complimentary region; used in synth. 100-mer #3 as replacement for R1P. | CTGGCGCGGGCATGACTCC | Bases rearranged to create unique site for primer binding; 3' C residue marks RNA initiation site. | A + G = 10<br>G + C = 14 |
| T7<br>T7 RNA polymerase promoter sequence | TATAGTGAGTCGTATTAAAG | T7 promoter sequence modified at 3' end to be compatible with cloning into pUC19/Hind III. | N/A |

EXAMPLE 2

CONSTRUCTION, STRUCTURE AND CLONING OF A PRECISELY EXCISABLE CONCATAMERIC INSERT FOR THE GENERATION, BY PARTIAL RESTRICTION DIGESTION, OF BOTH 100 bp and 20 bp dsDNA LADDERS One embodiment of the invention includes the creation of a dsDNA multimer that provided the material (after appropriate concatamerication and amplification by cloning) for a dsDNA ladder according to the "excision cassette method" described in FIG. 1, #3a).

The 'cassette' subunit was constructed as shown in FIG. 2a by first synthesizing an upper strand with the 100 nt sequence represented by the five 20 nt elements R1D-A-Sm-A'-R1P in linear order. Short 3' and 5' sequence base extensions were used to facilitate primer binding for the process of making the oligomer double-stranded. Elements R1D (EcoR1-distal) and R1P (EcoR1-proximal) contribute the two EcoR1 excision sites. A and A' represent two versions of prototypic elements with an internal sequence of exclusively Gs and Ts and the AluI site-generating terminal dinucleotides. Element Sm contributes the midpoint (50 bp from each terminus) SmaI concatamer insertion site (see FIG. 1, #3a). A SmaI site was chosen for this purpose because it cuts with blunt ends to accept the blunt-ended concatamerized multimers. Note that the SmaI site (CCCGGG) unavoidably introduces extraneous C residues at non-ladder positions, which affect the 3'-deoxy G-generated RNA ladder, however, these sequences eventually end up at the extreme distal end of the ladder, at positions 951, 952, and 953, where they detract minimally from its functionality. The cassette 100-mer (100-mer #1) was made double stranded by annealing a 24 base synthetic primer at its 3' end and extending the primer with Klenow fragment of DNA polymerase. The resulting 128 bp fragment was cleaved to the 100-mer cassette size with EcoR1 and cloned into the EcoR1 site of pUC19* (a derivative of pUC19, in which the HindIII site was removed) (FIG. 2b).

A second 100-mer subunit (FIG. 2, 100-mer #2) was constructed by oligonucleotide synthesis of both the upper and lower strands, according to the sequence represented by the elements ED-A-HIII-A-A-EP in linear order. The HIII-A junction created the unique HindIII site at the midpoint of this subunit. This HindIII site provides the second selectable cleavage site (and also a unique AA dinucleotide) at the 100 nt "landmark interval-determining" positions. Addition of the ED and EP 10 nt element made the subunit halves equal to 50 bp on both sides of the HindIII site. The construction strategy used here was to initially clone a dimer of this sequence into the SmaI site of the cassette (FIG. 2c), creating the plasmid designated pUC19*-ds300 containing three 100-mer subunits—in linear order: R1D-A-SmD/Ed-A-HIII, A-A-EP/ED-A-HIII, and A-A-EP/SmP-A'-R1P (FIG. 2d). The middle subunit is cleavable with HindIII, and is referred to as the basic 'sticky end' 100-mer fragment. This fragment represents the prototypic embodiment of the 100-nucleotide multimer reagent of the invention, and was the one actually used for the subsequent building up of the all the ladder inserts (dsDNA, ssDNA, and RNA) to their final 1000 bp size—i.e. by repeated cloning into one of the HindIII sites (cleaved by partial HindIII digestion) of the growing concatamers. A pUC19*-ds200 clone, having a single unique HindIII site, was also derived by removal of the 'sticky end' 100-mer fragment from pUC19*-ds300.

In the pUC19*-dsXXX family of plasmids (where XXX is 100, 200, etc . . . 1000), the complete 100, 200, etc . . . 1000 bp inserts, respectively, are precisely excisable by digestion with EcoR1. These purified inserts yield 100 bp ladders upon partial digestion with HindIII, and 20 bp ladders upon partial digestion with AluI (see FIG. 4a).

In summary, FIG. 2 shows: a) A 120-mer template and a 24-mer primer oligonucleotide with the indicated sequences (synthesized on the Pharmacia Gene Assembler). The two oligomers were annealed and the primer was extended in the presence of four dNTPs and Klenow fragment of DNA polymerase according to standard methods (Ausubel, et al., eds. *Current Protocols in Molecular Biology*, supra), and then the dsDNA fragment was cleaved at its two terminal EcoRI sites. b) The 100 bp fragment obtained in (a) (100-mer #1) was cloned into the EcoRI site of PUC19*, a derivative of pUC19 in which the HindIII site had been removed. c) A blunt-ended 100 bp fragment (100-mer #2) was prepared by oligonucleotide synthesis of the complete upper and lower strands on the Gene Assembler, and their subsequent annealing. The recombinant plasmid pUC19*/100-mer #1 was cleaved at the SmaI site in the center of the 100-mer #1 fragment and phosphatase to minimize vector recircularization. Phosphorylated fragment 100-mer #2 was then cloned into this site. d) The cloning described in (c) resulted in the recovery of structure pUC19*-ds300, in which a dimer of 100-mer #2 had been inserted into the pUC19*/100-mer #1 vector. The head-to-tail orientation of all elements was confirmed by sequencing. A 251 bp BglI-HindIII fragment was excised for use in construction of the pGEM-3Zf(-)-ssDR200 structure. A 100 bp HindIII 'sticky end' fragment was also excised by HindIII digestion, and purified on an agarose gel for use in the step-by-step building up of a 1000 bp head-to-tail multimeric structure.

EXAMPLE 3

CONSTRUCTION, STRUCTURE, AND CLONING OF A SEQUENCING PRIMER-BINDING AND T7 PROMOTER-CONTAINING TEMPLATE FOR THE GENERATION OF ssDNA AND RNA 20-BASE LADDERS BY 3'DEOXY CHAIN TERMINATION.

In further embodiments of the invention, the reagent is useful as the template for generating RNA or ssDNA ladders when used with an RNA polymerase promoter or oligonucleotide primer binding site, respectively.

When the multimer reagent has "landmark interval-determining" features at larger intervals than the basic subunit interval (e.g., a second restriction endonuclease cleavage site at 100 nt intervals, or a di- or tri- interval-determining nucleotide every 1000 nt), and when such features fall at the termini of the basic multimer (as described in Examples 1 and 2), it is necessary to clone the basic multimer reagent into a "cassette" version of the multimer in which the RNA-IS corresponds to base #1. It is also necessary for the sequence of the first subunit of the cassette multimer to be modified to create a unique primer binding site, wherein the 5'-terminus of the priming oligonucleotide can be made to correspond to base #1 of the multimer. Other, unsatisfactory, RNA-IS and priming positions (i.e., those merely flanking, and "in register" with, the multimer) would make these "landmarks" fall in the wrong position in the ladder, for example at positions 120, 220, 320, etc., instead of 100, 200, 300, etc.

Figure 3:
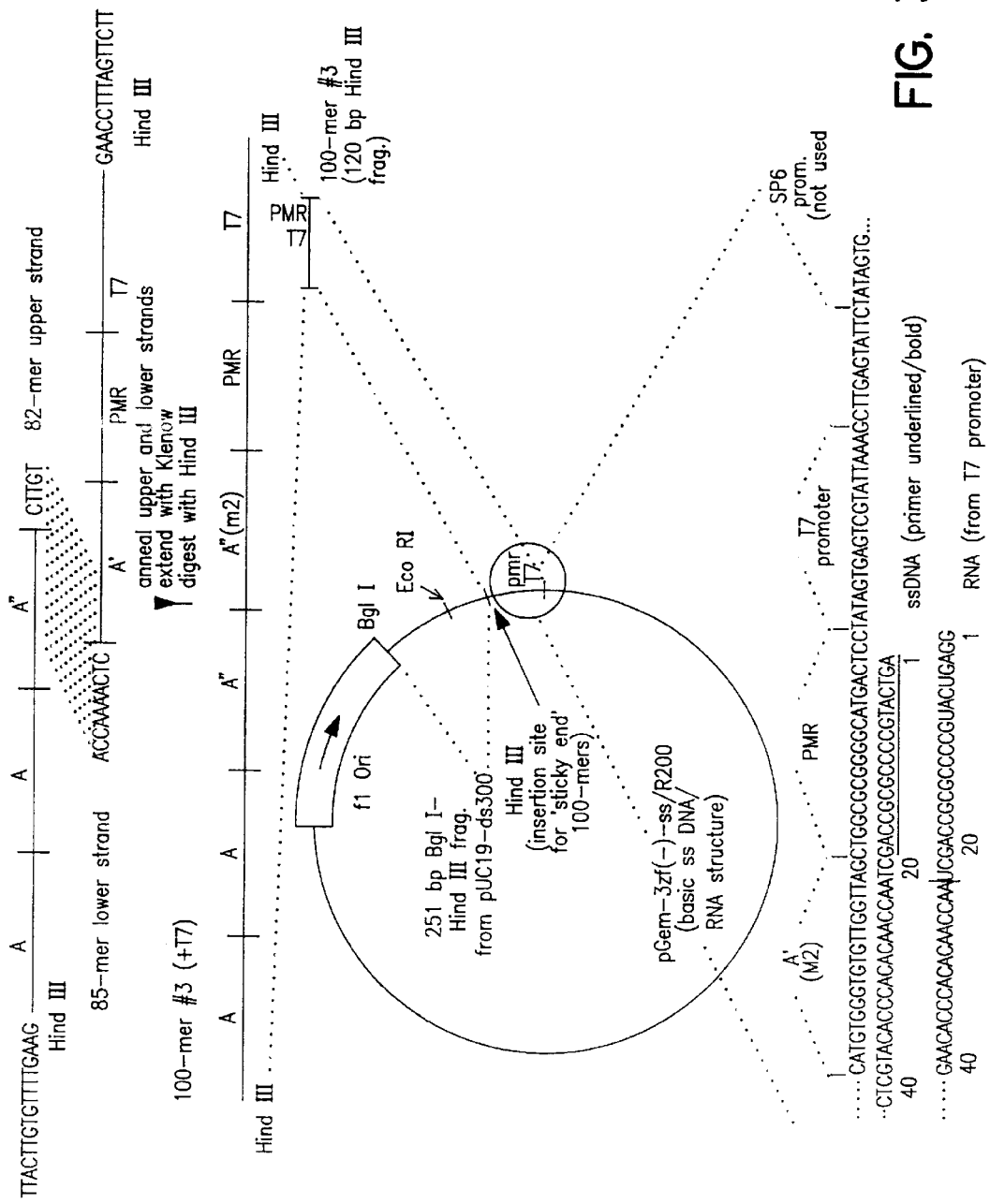
FIG. 3 shows the construction, structure, and cloning of a sequencing primer-binding, and 17 promoter-containing, template for the generation of 20-base ladders of ssDNA and RNA by 3'deoxy chain termination (SEQ ID NOS. 17, 18, 19 and 20).

In order to introduce a unique sequencing primer binding element (PMR in Table 1) and T7 promoter element (T7 in Table 1) at the proximal end of the basic ladder template described in Examples 1 and 2, the strategy outlined in FIG. 3 was used. Briefly, a third 100-mer subunit (100-mer #3) containing these structural features (actually, a 120-mer with the 20 bp T7 element: i.e., A-A-EP/SmP'-A'-PMR-T7) was constructed by first synthesizing an 82-base upper strand and an 85-base lower strand on the Gene Assembler (Pharmacia). The strands were designed to be complimentary over a 15 bp overlapping stretch and, in addition, had 17 bp and 15 bp 5' extensions, respectively, to allow for efficient cleavage at the terminal HindIII sites (FIG. 3a). The two strands were annealed and extended with Klenow fragment of DNA polymerase, and the resulting 152 bp fragment was cleaved with HindIII to yield a 120 bp fragment, 100-mer #3 (+T7) (FIG. 3b)

An f1 Ori-containing plasmid, pGEM-3Zf(-), (Promega Corp) was chosen as the cloning vector for this construction, since it allows the production of single-stranded DNA, if desired, for use in the dideoxy sequencing procedure. The vector was cleaved at its HindIII site and its BglII site located just at the end of the f1 Ori region. The homologous BglI site from pUC19*-ds300 was used to remove a 251 bp fragment from that vector, and this fragment was cloned into the pGEM-3Zf(-) vector (FIG. 3c). Since homologous BglI sites were used, the cloning completely maintained the integrity of both the f1 Ori and β-gal reading frame of the pGEM vector. Also transferred as part of the 251 bp fragment was the distal 100 bp ladder subunit from pUC19*-ds300: R1D-A-SmD/ED-A-HIII. This subunit provided a unique "in register" terminal truncation site (EcoR1), which is desirable in a template to be used for in vitro transcription, and required for synthesis of an RNA to be used for ladder generation by, e.g., RNase T1 digestion.

To complete the basic ssDNA/RNA template construction, the 100-mer #3 (+T7) in FIG. 3b was cloned in the proper orientation into the HindIII site of the modified pGEM-3Zf(-) vector, producing the construct, pGEM-3Zf(-)-ssR200 (FIG. 3c). The proximal 100 bp ladder subunit of the new construct has an adjacent T7 promoter region, and, in addition, it has a unique PMR element replacing the R1 P element of the dsDNA ladder structure, eliminating the unwanted proximal EcoR1 site. The original T7 promoter of the pGEM vector was eliminated by replacement of the BglI/HindIII fragment; however, the vector still has its SP6 promoter which is immediately downstream of the new T7 promoter. This SP6 promoter is not used in any ladder-generating function. The PMR element was designed to have equal purines and pyrimidines, but with the substitution of some Ts with Cs and some Gs with As, to create an element that would selectively bind a homologous sequencing primer.

As shown in FIG. 3d, in the pGEM-3Zf(−)ssDRXXX family of plasmids (where XXX is 100, 200, etc . . . 1000), DNA sequencing reactions initiated by the 18-mer primer (underlined bold) in the presence of dideoxy TTP show a single band, derived from the 'A' in the AluI recognition sequence, marking every 20 nt interval (i.e. at positions 20, 40, 60, 80, etc . . . 980); a double band, derived from the 'AA' in the HindIII recognition sequence, marking every 100 nt interval (i.e. at positions 100–101, 200–201, 300–301, etc . . . 900–901); and, finally, a double band, derived from the 'AA' of the EcoRI site, at positions 999–1000. Similarly, RNA synthesized from the T7 promoter, in the presence of the RNA chain terminator 3'deoxy GTP (Parvin, et al., supra), show single bands, derived from the 'C' in the AluI and HindIII recognition sequences, marking every 20 nt interval (i.e. at positions 20, 40, 60, 80, etc . . . 980); and from the 'C' of the EcoRI site at position 998. Extraneous bands derived from the SmaI site of the original cassette structure (FIG. 2a) are also be present at positions 951, 952, and 953. Truncation of the plasmid template at the unique EcoRI site cause those RNA transcripts not prematurely terminated by incorporation of 3'deoxy GTP to end at position 1002.

EXAMPLE 4

BUILDING UP OF LADDER TEMPLATES TO 1000 bp CONCATAMERS AND PRODUCTION OF THE LADDERS

In order to build up both basic structures, pGEM-3Zf(−)-ssDR200 and pUC19*-ds200, to the full 1000 bp insert size, the former construct was partially digested with HindIII, and 'sticky-end' HindIII 100-mer fragments were cloned into the internal HindIII site in sequential cycles, until the 1000 bp insert size was reached. All subclones were analyzed by sequencing, and only those with fragments inserted in a head-to-tail orientation were used. This was necessary for the function of the ssDNA and RNA ladder templates (but not important for the function of the dsDNA template). From the final construct, pGEM-3Zf(−)-ssDR1000, a partial HindIII digest was performed to remove an 800 bp fragment, which was the cloned into the HindIII site of the pUC19*-ds200 plasmid, completing its construction to pUC19*-ds1000.

Figures 4A, 4B, 4C:
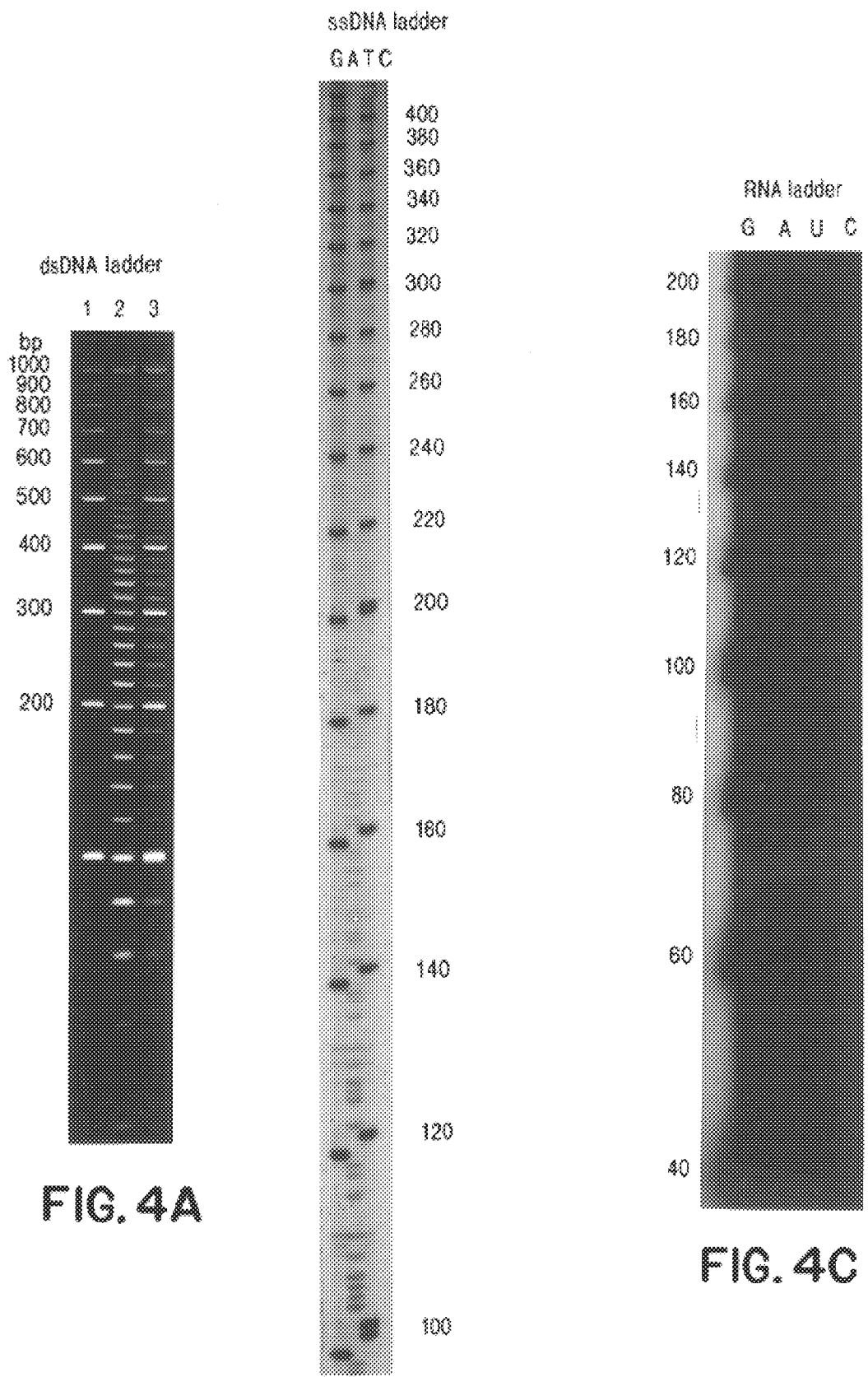
FIG. 4a shows a dsDNA ladder of the invention. Lane 1, HindIII (100 bp ladder; Lane 2, AluI (20 bp ladder); lane 3, HindIII and AluI (100 bp/20 bp ladder).
FIG. 4b shows a ssDNA ladder of the invention (lanes G,A,T,C).
FIG. 4c shows an RNA ladder of the invention (lanes G,A,U,C).

For preparation of the dsDNA ladder (FIG. 4a), the recombinant plasmid, pUC19*-ds1000 was digested with EcoRI and the 1000 bp insert fragment was purified by agarose gel electrophoresis. This fragment was subjected to partial digestion with either HindIII (5 μg fragment, 0.5 units HindIII, 60 min) or AluI (10 μg fragment, 0.1 units AluI, 20 min) under standard reaction conditions. The reactions were stopped by addition of EDTA to 20 mM and aliquots loaded onto a 3% NuSleve 3:1 (FMC BioProducts) agarose gel in 1×TBE buffer. Electrophoresis was at 6V/cm for 2.5 hrs. FIG. 4a shows the ladders generated: lane 1, HindIII digest (100 bp ladder); lane 2, AluI digest (20 bp ladder); lane 3, HindIII and AluI digests combined (100 bp/20 bp ladder).

For preparation of the ssDNA and RNA ladders (FIG. 4b and 4c, respectively), the recombinant plasmid, pGEM-3Zf (−)-ss/R500 was used. For the ssDNA ladder, the recombinant plasmid was denatured in alkalai according to standard protocols (Promega Corp.), combined with specific primer (see FIG. 3d) and subjected to sequencing reactions in the presence of 32-P-ATP as the radiolabel, and dideoxy GTP, ATP, TTP, and CTP as the chain terminators (FIG. 4b, lanes G,A,T, and C). The G and T reactions correspond to the C and A 'interval-determining' nucleotides of the template multimer. The T reaction is 'in register' with the 5'-terminus of the primer, and produces the correct size marker ladder, with steps every 20 nt, up to 400 nt, upon electrophoresis in a 5% denaturing polyacrylamide sequencing gel, as shown. 100 nt intervals are marked by the double band corresponding to the AA dinucleotide in the HindII recognition sequence.

For the RNA ladder, the recombinant plasmid was combined in standard in vitro transcription reactions (Promega Corp.) with T7 RNA polymerase, the four NTPs according to the modification of Parvin, et al., (ITP, ATP, UTP, and CTP), 32-P-UTP as the radiolabel, and either 3'-deoxy GTP, ATP, UTP, or CTP as the chain terminators (FIG. 4c, lanes G,A,U, and C). The G and U reactions correspond to the C and A 'interval-determining' nucleotides of the template multimer. The G reaction is 'in register' with the RNA-IS of the template, and produces the correct size marker ladder, with steps every 20 nt, up to 200 nt, on a 6% denaturing polyacrylamide gel, as shown. With the multimer reagent of these examples, the 100 nt intervals are not specifically marked in the G lane used for the RNA ladder. Other examples of this ladder have been produced in which the 100 nt intervals are accentuated by adding to the gel an aliquot of a standard transcription reaction using partial HindIII-truncated multimer as the template.

Although the invention has been described with reference to the presently preferred embodiment, it should be understood that various modifications can be made without departing from the spirit of the invention. Accordingly, the invention is limited only by the following claims.

SUMMARY OF SEQUENCES

SEQ ID NO:1 is the nucleotide sequence of a basic 20-mer subunit, A.
SEQ ID NO:2 is the nucleotide sequence of a basic 20-mer subunit, A'.
SEQ ID NO:3 is the nucleotide sequence of a basic 20-mer subunit, A".
SEQ ID NO:4 is the nucleotide sequence of a basic 20-mer subunit, R1D.
SEQ ID NO:5 is the nucleotide sequence of a basic 20-mer subunit, R1P.
SEQ ID NO:6 is the nucleotide sequence of a basic 20-mer subunit, Sm.
SEQ ID NO:7 is the nucleotide sequence of the HindIII subunit of 100-mer #2.
SEQ ID NO:8 is the nucleotide sequence of the distal end of 100-mer #2.
SEQ ID NO:9 is the nucleotide sequence of the proximal end of 100-mer #2.
SEQ ID NO:10 is the nucleotide sequence of the proximal end/distal fusion product of 100-mer #2.
SEQ ID NO:11 is the nucleotide sequence of SmD/ED.
SEQ ID NO:12 is the nucleotide sequence of EP/SmP.
SEQ ID NO:13 is the nucleotide sequence of PMR.
SEQ ID NO:14 is the nucleotide sequence of T7 RNA polymerase promoter sequence.
SEQ ID NO:15 is the nucleotide sequence of the 5' EcoR1 subunit of 100-mer #1.
SEQ ID NO:16 is the nucleotide sequence of the 3' EcoR1 24-bp primer of 100-mer #1.
SEQ ID NO:17 is the nucleotide sequence of the 5' HindIII subunit of the 82-mer upper strand.
SEQ ID NO:18 is the nucleotide sequence of the 5' HindIII subunit of the 85-mer lower strand.
SEQ ID NO:19 is the nucleotide sequence of A', PMR, T7 promoter, and SP6 promoter.
SEQ ID NO:20 is the nucleotide sequence of the RNA synthesized from SEQ ID NO:19 from the T7 promoter.

I claim:

1. A nucleic acid multimer template for generating a size marker, wherein the template comprises:
   a) about 100 to 1000 nucleotides per nucleotide strand;
   b) wherein each nucleotide strand in the template has repeating nucleotide subunits of a defined length for production of defined size fragments;
   c) wherein said nucleotide subunits are separated by identical numbers of nucleotides;
   d) wherein each nucleotide subunit has a purine and pyrimidine content of about 50% each; and
   e) wherein said nucleotide subunits have nucleotides which are substantially non self-annealing.

2. The nucleic acid multimer template of claim 1, wherein the repeating nucleotide subunits are of a length, selected from the group consisting of 5, 10, 20, 25, 50 and 100 nucleotides.

3. The nucleic acid multimer template of claim 2, wherein the repeating nucleotide subunits are of a length selected from the group consisting of 10, 20, and 25 nucleotides.

4. The nucleic acid multimer template of claim 1, wherein the number of nucleotides that separate the nucleotide subunits is selected from the group consisting of 1, 2, and 3 nucleotides.

5. The nucleic acid multimer template of claim 4, wherein the nucleotides are selected from the group consisting of A, G, C, T, and analogs thereof.

6. The nucleic acid multimer template of claim 1, wherein the template is a single-stranded molecule.

7. The nucleic acid multimer template of claim 1, wherein the template is a double-stranded molecule.

8. The nucleic acid multimer template of claim 1, further comprising an oligonucleotide sequence at the 5'- or 3'-terminal end of the multimer, wherein the sequence has a different sequence from the repeating nucleotide subunits within the multimer.

9. The nucleic acid multimer template of claim 8, wherein the nucleic acid sequence contains an RNA polymerase promoter.

10. The nucleic acid multimer template of claim 8, wherein the nucleic acid sequence contains a primer binding site.

11. The nucleic acid multimer template of claim 9, wherein the RNA polymerase promoter is a bacteriophage promoter.

12. The nucleic acid multimer template of claim 11, wherein the bacteriophage promoter is selected from the group consisting of T3, T7, and SP6.

13. The nucleic acid multimer template of claim 1, wherein the nucleic acid size marker generated is DNA.

14. The nucleic acid multimer template of claim 1, wherein the nucleic acid size marker generated is RNA.

15. The nucleic acid multimer template of claim 14, wherein the RNA is cleavable by RNase T1.

16. The nucleic acid multimer template of claim 15, wherein the RNA is specifically cleavable at positions that separate the nucleotide subunits of the template.

17. The nucleic acid multimer template of claim 14, wherein the RNA is cleavable by 3' deoxy RNA chain termination.

18. The nucleic acid multimer template of claim 17, wherein the RNA is cleavable by incorporation of a specific 3' deoxy RNA within the template at positions that separate the nucleotide subunits.

19. The nucleic acid multimer template of claim 1, wherein the nucleic acid multimer template is inserted into a vector.

20. The nucleic acid multimer template of claim 19, wherein the vector is a plasmid.

21. The nucleic acid multimer template of claim 1, wherein the template further comprises a selectable cleavage site located at the positions that separate the nucleotide subunits of the template.

22. The nucleic acid multimer template of claim 21, wherein the selectable cleavage site is a restriction endonuclease site.

23. The nucleic acid multimer template of claim 21, wherein the template further comprises a second selectable cleavage site located at the positions that separate multiple nucleotide subunits at regular intervals.

24. A kit useful for generating the size determination of a nucleic acid, the kit consisting of carrier means being compartmentalized to receive in close confinement therein one or more containers consisting of a container containing the nucleic acid multimer template of claim 1.

25. The kit of claim 24, further comprising a container containing at least one deoxy NTP or NTP(s).

26. The kit of claim 25, wherein the deoxy NTP or NTP corresponds to the complement of the nucleotides that separate the nucleotide subunits of the nucleic acid multimer template of claim 1.

27. The kit of claim 24, further comprising a container containing an enzyme selected from the group consisting of a restriction enzyme and RNase.

28. The kit of claim 24, further comprising a container containing an oligonucleotide primer.

29. The kit of claim 28, wherein the 5'-terminal end of the primer is in operable linkage with the nucleic acid multimer template of claim 1.

* * * * *